United States Patent [19]

Jerman

[11] Patent Number: 5,824,204
[45] Date of Patent: Oct. 20, 1998

[54] MICROMACHINED CAPILLARY ELECTROPHORESIS DEVICE

[75] Inventor: John H. Jerman, Palo Alto, Calif.

[73] Assignee: IC Sensors, Inc., Milpitas, Calif.

[21] Appl. No.: 671,428

[22] Filed: Jun. 27, 1996

[51] Int. Cl.$^6$ ................................................. G01N 27/26
[52] U.S. Cl. .......................... 204/601; 422/99; 204/451
[58] Field of Search ................................. 216/2, 33, 39, 216/51, 56; 422/50, 99, 100, 236; 137/563; 204/451, 601; 347/20

[56] References Cited

U.S. PATENT DOCUMENTS

| | | | |
|---|---|---|---|
| 4,908,112 | 3/1990 | Pace | 210/198.2 |
| 4,994,141 | 2/1991 | Harms et al. | 216/2 |
| 5,194,133 | 3/1993 | Clark et al. | 204/608 |
| 5,262,127 | 11/1993 | Wise et al. | 422/98 |
| 5,314,458 | 5/1994 | Najafi et al. | 607/116 |
| 5,385,709 | 1/1995 | Wise et al. | 422/98 |
| 5,417,235 | 5/1995 | Wise et al. | 137/1 |

OTHER PUBLICATIONS

E. Bassous ("Fabrication Process for Precise COntrol of Nozzle Dimensions", IBM Technical Disclosure Bulletin, vol. 20, No. 6, Nov. 1977).

T.R. Albrecht et al., "Microfabrication of cantilever styli for the atomic force microscope", J. Vac. Sci. Technol. A., vol. 8, No. 4, Jul./Aug. 1990, pp. 3389–3392.

D. Jed Harrison et al., "Chemical Analysis and Electrophoresis Systems Integrated on Glass", IEEE Hilton Head, 1992, pp. 110–113.

D. Jed Harrison et al., "Towards miniaturized electrophoresis and chemical analysis systems on silicon: an alternative to chemical sensors", Sensors and Actuators B. 10 (1993), pp. 107–116.

Howard J. Goldner, "Got a Tough Separation? Try Capillary Electrophoresis", R&D Magazine, Jun. 1991, pp. 28–34.

*Primary Examiner*—Kathryn L. Gorgos
*Assistant Examiner*—Alex Noguerola
*Attorney, Agent, or Firm*—Skjerven, Morrill, MacPherson, Franklin & Friel LLP; Norman R. Klivans

[57] ABSTRACT

A micromachined structure for handling fluids with an applied high voltage, i.e. for electrophoresis, includes a glass or other highly insulative substrate on which are formed very small diameter capillary channels of e.g. silicon nitride. Due to the absence of a silicon substrate, this structure is highly electrically insulative. The silicon nitride channels are formed by a micro-machining and etch process, so that they are initially defined in an etched sacrificial silicon wafer by conformal coating of etched features in the silicon wafer with a silicon nitride layer, which is then patterned to define the desired channels. The silicon wafer is bonded to the glass substrate and the bulk of the silicon wafer is sacrificially etched away, leaving the desired silicon nitride channels with supporting silicon mesas. The remaining silicon nitride "shell" is bonded to the glass substrate and substantially duplicates the etched features in the original silicon wafer. The capillary channels are of a material such as low stress silicon nitride and there is no electrical shorting path to the highly insulative glass substrate.

16 Claims, 3 Drawing Sheets

MICROMACHINED CAPILLARY ELECTROPHORESIS DEVICE

BACKGROUND OF THE INVENTION

1. Field of the Invention

This invention relates to micromachined devices and more particularly to a micromachined fluid handling device suitable for application of high voltages.

2. Description of the Prior Art

Electrophoresis is a well known technique for separating complex organic compounds due to their different mobilities in a carrier. An electric field is created in an ionic liquid, and the electric field tends to pump the liquid. The velocity of a particular sample component through a capillary column is a function of the electric field strength, the movement of the carrier liquid, and the electrical mobility of the sample component.

Current laboratory instrumentation for separation of organic material uses electrophoresis, either in the form of a thin planar gel or in an enclosed capillary tube. The separation lengths employed typically range from 20 to 50 cm for gels, and up to a 1 or 2 meters for capillaries. The voltages to perform these separations at maximum efficiencies are large, e.g. 5 to 50 kilovolts. The most efficient separations tend to be at the highest voltages, just below the point where heating caused by electrical power dissipation in the gel creates difficulties from gas generation, differential mobilities caused by temperature gradients, or sample degradation. Typically the separation of the constituents of a sample is by differential migration through the gel or column due to charge to size ratios or by chemical interactions between the sample and a stationary phase in the column or gel. The efficiency of separation is improved by the reduction in capillary diameter or thickness of a planar gel.

Micromachining is a well known process using semiconductor fabrication techniques including photolithography, etching, and layer deposition to fabricate microstructures such as fluid manifolds, flow sensors, and detectors. Prior art electrophoresis devices have been made using silicon micromachining techniques to fabricate miniature separation channels, sample injection regions, and detection chambers in a silicon "chip" for electrophoretic analysis. These devices minimize the size and/or cost of the instrumentation. See Pace U.S. Pat. No. 4,908,112 disclosing the combination of an etched channel in a silicon wafer and a cover to make an enclosed capillary tube. A series of electrodes create a high local electric field in the capillary while minimizing the total voltage drop between the interior of the capillary and the silicon substrate.

Silicon is a semiconductor material that is effectively an electrical conductor at room temperature. Hence large voltages along the capillary channel must be insulated from the silicon substrate by an insulating (dielectric) layer, typically silicon dioxide or silicon nitride. These materials can be deposited in layers up to e.g. 10 $\mu$m thick using conventional processing techniques. Even at these thicknesses, the maximum voltage withstood without electrical breakdown is only about 2 kilovolts which is well below the level desired for electrophoretic devices. Of more concern, however, is that any defect in the dielectric layer caused, for example, by a particle present during the deposition process, may reduce that breakdown voltage to very small levels, rendering the device useless.

A. Manz, et. al. in "Planar chips technology for miniaturization and integration of separation techniques into monitoring systems, Capillary electrophoresis on a chip", *J. of Chromatography*, Vol. 593, pp. 253–258, 1992, discloses a device of this type using a passivated (insulated) channel formed in a silicon wafer having an upper voltage limit of only 900 V, resulting in poor separation efficiency. Because of this low voltage limit of silicon, other devices have typically been fabricated instead in electrically insulating substrates such as glass or fused silica, which can withstand high voltages without breakdown. However, etching of these structures in glass is difficult due to the limited isotropic nature of the etchants needed to etch the glass. This limits the geometries of the etched features, in contrast to the use of plasma etchants and anisotropic liquid etchants in silicon wafers which result in a wide variety of etched geometries using well established and easily controlled etching processes and equipment.

Therefore the prior art in micromachined electrophoresis devices is limited to (a) low voltage easily fabricated silicon devices; or (b) high voltage glass or silica devices which cannot be fabricated to provide the needed features in terms of channels, chambers, etc.

SUMMARY

The above-described limitations of prior art micromachined electrophoresis devices are overcome with the present method and device. The present invention is directed to a fluid handling structure comprising a planar substrate of a first dielectric material and having a principal surface; and a plurality of channel structures formed on the principal surface, each channel structure extending from the principal surface and being of a second differing dielectric material, and defining a fluid-carrying channel between the channel structure and the principal surface. In a method to fabricate the present device, first one etches the desired groove, chamber, and through-hole features in the surface of a sacrificial silicon wafer using conventional micromachining etching techniques, e.g. anisotropic and isotropic plasma and wet chemical etchants. A layer of e.g. a silicon-rich or low stress silicon nitride material, e.g. 0.5 $\mu$m thick (and generally less than 5 $\mu$m thick), is deposited onto the wafer surface, conformally coating the etched features and then is photolithographically patterned to define various silicon nitride features. The silicon wafer is then bonded to an insulating substrate of, for instance, glass (Pyrex) using e.g. adhesives or anodic bonding. It is to be understood that other materials can be used; e.g. the channels may be of silicon dioxide or a polymer such as polyamide and the substrate can be of fused silica or plastic.

All (or selected portions) of the silicon wafer are then removed (sacrificed) using etchants, which selectively do not substantially etch either the glass substrate or the nitride layer. A silicon nitride "shell" then remains bonded to the glass substrate, and the shell substantially duplicates the etched geometries in the sacrificial silicon wafer. The silicon wafer may be etched away only partly by masking portions of its backside surface with a silicon nitride layer prior to removal of the bulk silicon. The resulting nitride channels are e.g. 10 to 50 $\mu$m wide and 15 to 20 $\mu$m deep, thus being strong even though having very thin silicon nitride walls.

Also in accordance with this invention the silicon wafer is micromachined to define other structures therein, such as silicon mesas surrounding for instance a reaction or detection chamber, as well as other conventional features such as inlets and outlets for fluids. All of these features are preserved when the remainder of the silicon wafer is etched away. Also in accordance with the invention a layer of e.g.

an insulating polymer is applied to the surface of the glass substrate for insulative (thermal, electrical, or mechanical protective) purposes. Usually, one wants to have high heat conduction to remove heat from the channel which is the separation column, but one also may want to thermally insulate the heated reaction chambers.

BRIEF DESCRIPTION OF THE DRAWINGS

Identical reference numerals in various figures refer to similar or identical structures.

DETAILED DESCRIPTION

The present device includes a capillary (small diameter) channel structure of a material such as low stress silicon nitride, with the sacrificial silicon wafer having been mostly or totally etched away, so there is no longer an electrical shorting path through the silicon wafer. Thereby, the maximum electrophoresis voltage that can be applied is similar as with fused silica capillary columns (non-micromachined components), and is typically limited only by heating in the carrier liquid.

Figure 1:
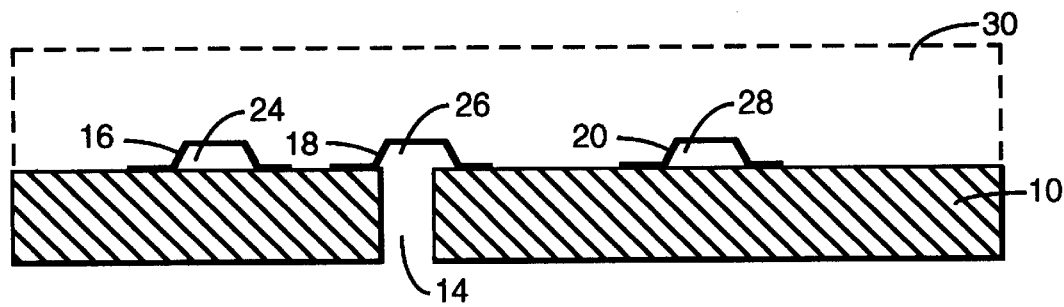
FIG. 1 shows a simplified cross-sectional view of a device in accordance with the present invention.

FIG. 1 is a simplified cross-sectional view of a device in accordance with this invention. It is to be understood that FIG. 1 is not to scale; the actual dimensions of the device would be those typical of micromachined devices; FIG. 1 emphasizes relevant features. A glass (e.g. PYREX) substrate 10 defining, in this example, a through-hole 14, has formed on its surface a plurality of nitride channel structures 16, 18, and 20, these structures respectively enclosing internal channels 24, 26 and 28; hence the channels 24, 26, 28 are the regions between the (hollow) nitride structures 16, 18, 20 and the underlying glass substrate 10. For purposes of this illustration, and not present in the actual finished device, the outline of the sacrificed silicon wafer 30 is shown.

Figure 2A:
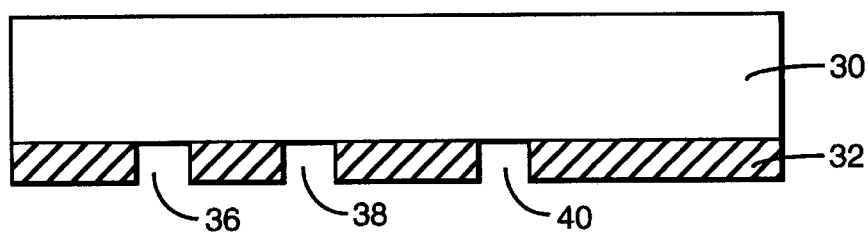
FIGS. 2A–2F show in cross-sectional views steps in fabricating the device of FIG. 1.
Figure 2B:
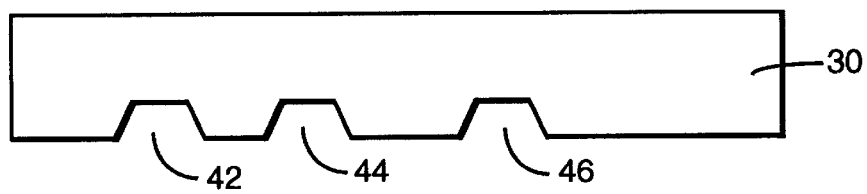
Figure 2C:
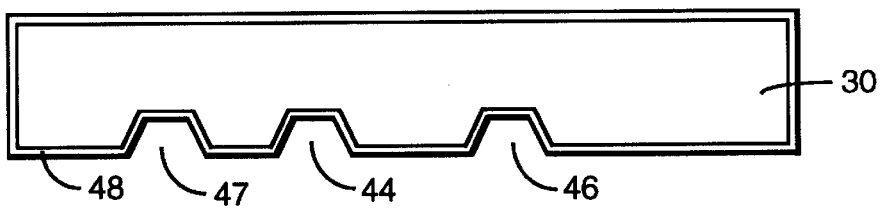
Figure 2D:
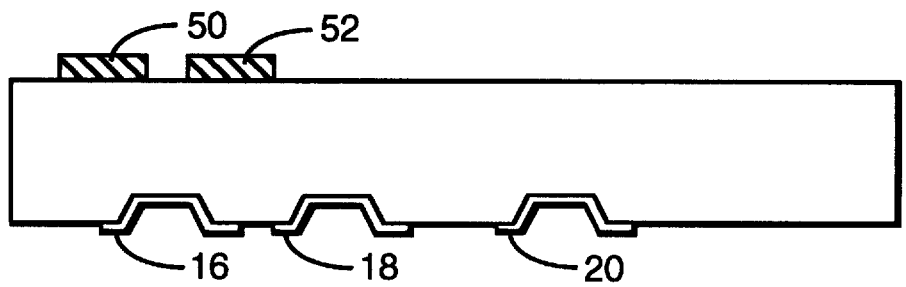
Figure 2E:
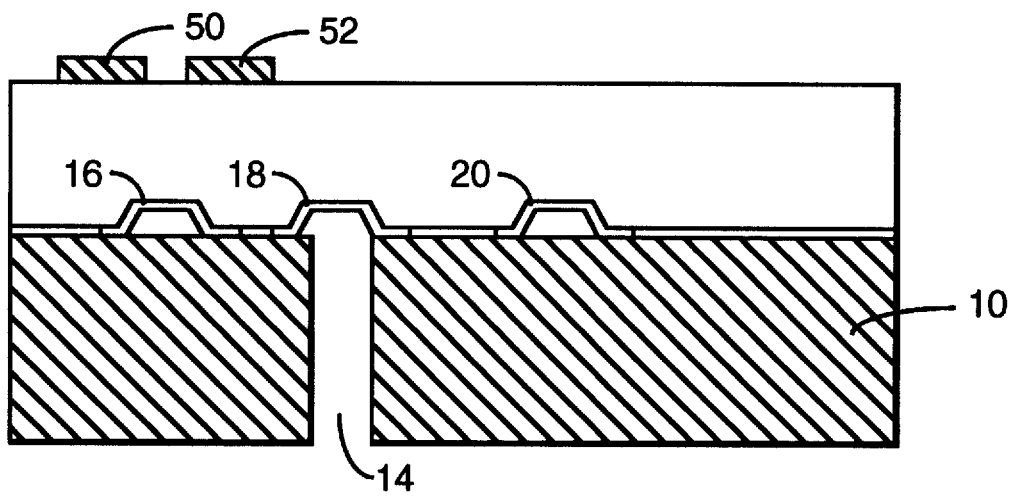

An exemplary fabrication process for this device is as follows:

1. A silicon wafer 30 as shown in FIG. 2A, typically of 100 surface orientation, has a mask layer formed on its principal surface by, for example, thermally growing a layer of silicon dioxide 32 on the wafer 30 surface. (It is to be understood that FIGS. 2A to 2F show only a small portion of a silicon wafer.)
2. The mask layer 32 is patterned by e.g. conventional photolithography and a subsequent oxide etch with an HF-based oxide etchant to define openings 36, 38, 40.
3. The silicon wafer 30 is etched using e.g. a mixture of KOH and water at 60° C. to produce v-groove(s) (not shown) or by plasma etching to produce u-grooves 42, 44, 46 with flat bottoms and sloping sides. The grooves are e.g. 5 μm to 300 μm deep and 5 μm to 300 μm wide.
4. The etch mask layer 32 is stripped using an HF-based oxide etchant, resulting in the structure of FIG. 2B.
5. A low stress (silicon-rich) silicon nitride layer 48 (see FIG. 2C) is deposited, e.g. using a LPCVD reactor, to a thickness of e.g. 0.2 to 5 μm (typically 0.2 to 2 μm). This silicon nitride layer 48 conformally covers the etched features 42, 44, 46, and typically covers both surfaces of the silicon wafer as in FIG. 2C.
6. The silicon nitride layer 48 is patterned by photolithography and a subsequent plasma etch using e.g. a $CF_4$ and oxygen plasma. Patterning the silicon nitride layer 48 on the wafer 30 backside (the surface opposite the previously etched grooves 42, 44, 46) defines the silicon regions to be etched away in the next step. Silicon nitride areas 50, 52 left on the backside surface define underlying silicon regions that will not be etched away, resulting in silicon "mesa" areas, as described below. The remaining portions of nitride layer 48 in the grooves are channel structures 16, 18, 20.
7. The silicon nitride layer is partially oxidized by a high temperature oxidation step at, for example, 1000° C. for 1 hour in a steam ambient.
8. The silicon wafer 30 is e.g. anodically bonded at its front side to PYREX™ (glass) plate 10 (see FIG. 2E) at a temperature of about 400° C. The glass plate 10 may have a number of small diameter holes, e.g. hole 14, previously drilled in it using e.g. ultrasonic or laser drilling techniques, and may have metal electrodes (not shown) previously formed conventionally on one or both sides, which are e.g. a platinum thin film metallization.
9. The thermal oxide layer grown in step 7 is stripped using a mixture of hydrofluoric acid and water. The silicon wafer 30 and glass plate 10 assembly is then placed in a silicon etch solution such as KOH and water at, for example, 80° C., and the entire thickness of the silicon wafer 30 is etched away. The etchant is selected to be one that does not significantly etch either the glass plate 10 or the silicon nitride structures 50, 52, 16, 18, 20.
10. The internal channels of resultant silicon nitride channel structures 16, 18, 20 are rinsed out to remove the etchant, leaving the structure of FIG. 2F which is similar to that of FIG. 1 but also having silicon mesas 58, 60.
11. A layer 66 of electrically insulating support material, such as polyamide, is optionally applied to the side of the glass plate 10 supporting the silicon nitride channel structures, to provide mechanical support for the silicon nitride channel structures 16, 18, 20.
12. The assembly is sawed (diced) into individual devices (not shown).

Figure 2F:
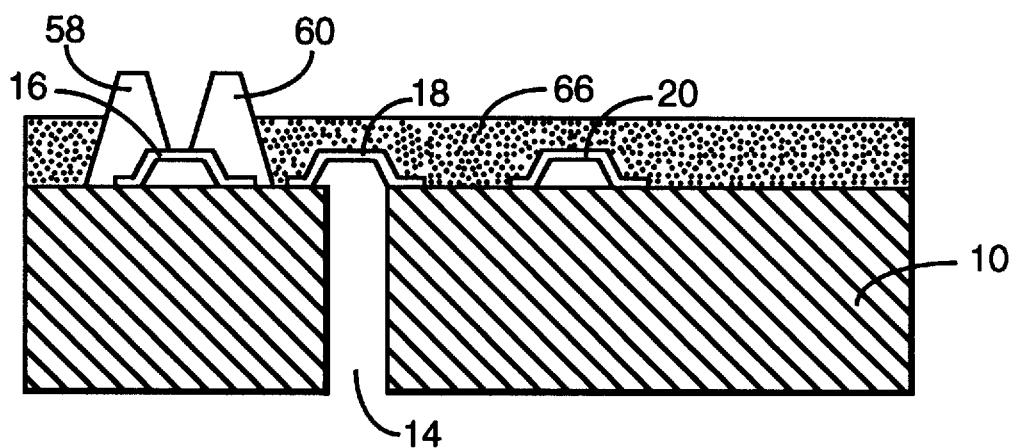
Figures 3A, 3B:
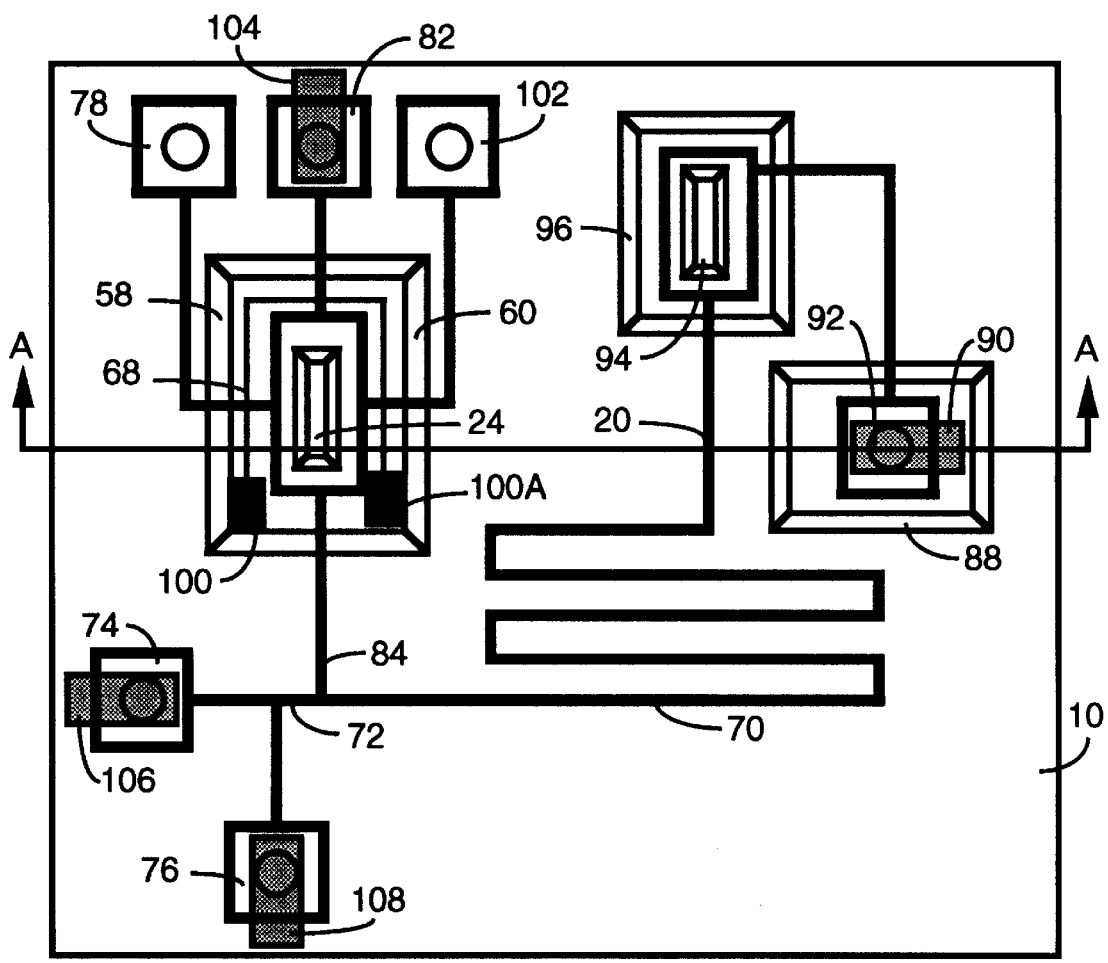
FIGS. 3A and 3B show respectively a plan view and a cross-sectional view of a capillary electrophoresis device in accordance with this invention.

A plan view of a more complex electrophoresis system (device) made using this process and including the features of FIGS. 1 and 2F is shown in FIG. 3A, and in cross-section along line A—A of FIG. 3A in FIG. 3B. This exemplary device includes a sample inlet, sample outlet, column inlet, column outlet and an injection region all on one chip. Typically a fluid sample is drawn in through the sample inlet 82 to sample channel 84, so a small volume of the sample is introduced to the separating column 70 at the intersection of the sample channel 84 and the separating column 70. The transport process used to move the sample through column 70 is either electroosmosis or pressure-driven physical pumping. The electrophoretic separation begins by applying high voltage along the separating column 70 by, for instance, electrodes 90 and 106 to create an electric field. (It is to be understood that two electrodes are needed for each electroosmotic pumping path, e.g. between electrodes 104 and 108.) A detection chamber 94 at the far end of the separating column 70 allows detection of the separated constituents, e.g. by optical methods such as by fluorescence using a conventional external detector (not shown).

A reaction chamber 24 is included in one embodiment to carry out the well known polymerase chain reaction (PCR)

process. In this process, segments of genetic material are duplicated in the presence of the appropriate enzymes and genetic bases sequentially as the temperature of the chamber is precisely cycled between certain temperatures, such as 55° C. and 95° C. At the higher temperature the appropriate enzyme breaks apart a double-stranded piece of genetic material. When the temperature is lowered, the individual strands combine with their complementary base pairs, duplicating the original genetic segment. This requires precise time and spatial control of the reaction chamber 24 temperature. In conventional (non-micromachined) instrumentation this requires relatively large heating and cooling systems.

In the present micromachined device, a suitable reaction chamber 24 is formed using the sacrificial silicon wafer process described above. The PCR reaction chamber 24 is substantially enclosed by a silicon mesa 58, 60 (as better illustrated in FIG. 3B). Silicon has a high thermal conductivity, nearly that of copper. Thus a silicon chamber provides efficient and substantially uniform heating of a liquid sample enclosed therein. (Note that structures 58 and 60 are two opposite sides of a single mesa.)

On the exterior surface of the silicon mesa 58, 60, there is a thin-film (metal) resistive heater trace 68, an electric current through which is conventionally controlled to obtain the desired temperatures. The temperature is sensed by e.g. measuring the resistance of the heater or a sensor element and inferred from the thermal coefficient of resistance of the metal of the element, or by an external thermistor or thermocouple.

It is often desirable to optically monitor the progress of the PCR process by, for example, monitoring fluorescent products of the reaction. This monitoring can be performed through a window 86 in mesa 58, 60 made from the back side of the sacrificial silicon wafer by defining the appropriate etch feature in the wafer backside nitride etch mask described above, or through the substrate 10.

Access holes 78, 82, 102 allow the introduction of the necessary reagents for the PCR process or other desired sample preparation step. These holes can also serve as outlets, e.g. for waste. The introduction of these reagents can also be by pressure-based pumping or by electroosmosis. After the desired reaction products are made, they are transported to the injection zone (the beginning of the separation column 70), followed by electrophoretic separation and subsequent detection.

Other features include a sample waste outlet 76, column inlet 74, column outlet 92, and electrical contact pads 100, 100A to the heater trace 68 for reaction chamber 24. Silicon mesa 88 surrounds the column outlet 92 which as shown in the cross section of FIG. 3B defines an access hole.

The electrodes 90, 104, 106, 108, providing the electric fields in the sample, can be placed where convenient, for example, on the glass plate 10 inside the entrance/exit holes, e.g. hole 14 in FIG. 1, by sputtering the appropriate metallization and defining the electrodes in the sputtered metal lithographically. Alternatively, discrete electrode probes are used by inserting these probes into the sample entrance/exit holes such as holes 74, 76, 78, 82, 92, 102 rather than using sputtered electrodes. If it is not convenient to provide access holes in the glass substrate, access holes such as hole 92 can be provided through the silicon mesas by providing a feature similar to a window as described in a silicon mesa, but also removing the silicon nitride from the front (channel) side by a lithography step and an etching step. Electrodes for the electrophoresis and electroosmosis processes can also be applied to the backside of the glass plate 10 and make electrical contact to the fluids through these access holes, as shown for electrode 90 in FIG. 3A.

Silicon mesa regions can also be provided around other features on the system, such as mesa 96 around detection chamber 94, and around the sample entrance/exit holes if needed to provide additional physical strength in those areas. The strength of the silicon nitride structures themselves is limited, so the insulating polymer layer 66 and/or silicon mesas allow the formation of larger silicon nitride structures. Also, the larger silicon nitride structures can be reenforced by internal support posts formed of silicon nitride extending from the surface of the glass substrate to the "roof" of the silicon nitride structures, and formed along with the remainder of the silicon nitride structures by defining additional appropriate features on the sacrificial silicon wafer.

A plurality of various features of the device can be provided on a single "chip" to allow more extensive sample analysis. For example, multiple reaction chambers can be provided, connected either in series or in parallel to the separating column to perform multiple sample preparation steps or to use one separating column for the analysis of reaction products from a number of different samples. Multiple separating columns can be connected on one chip to one reaction chamber to perform, for example, sequential separations from a single sample. A separating column can be used to separate sample components before introduction into a reaction chamber, thus allowing a reaction to be performed on a selected fraction of a sample. The products of that reaction can then be further separated by another column and subsequently detected.

Fluid connections to the device can be made using mechanical clamping with a gasket providing a seal around the access holes, e.g. holes 74, 76, 78, 82, 92, 102. These connections can be made either to glass plate 10 or on the side of the device on which the silicon nitride features are formed, to facilitate optical detection through the glass plate 10 or through windows in the silicon nitride structures. The critical, small volume regions are part of the device ("on chip"), thereby allowing the fluid connections to be made with non-critical, conventionally machined orifices and tubes.

It is of course advantageous if all components exposed to biological samples are disposable. In the integrated device of FIG. 3A, the sample inlet, reaction chamber, and separating column and detector are all on one chip, making disposal both economically feasible and convenient. The cost of such a chip is low since the expensive optical detection components are separate parts of the system ("off chip") and hence do not come in contact with the biological sample, and need not be disposed of after sample analysis.

A device as in FIG. 3A and having an exemplary size of 3 mm by 3 mm, is capable of withstanding an electrophoretic voltage of 10 kilovolts applied between electrode pairs, e.g. electrodes 90 and 106.

Instead of a PYREX substrate (glass plate), fused silica or other suitable material may be used. Also instead of an anodic bond, fusion bonding may be used. Alternative materials for the silicon nitride channels include aluminum oxide, titanium nitrate, or other nitrides, diamond, carbides (e.g. silicon carbide), or oxides of metals including for instance silicon dioxide; typically materials having a metallic ion and a dielectric are suitable, as are polymers such as polyamide, with appropriate changes to the etching of the silicon sacrificial wafer.

This disclosure is illustrative and not limiting; further modifications will be apparent to one skilled in the art in light of this disclosure and are intended to fall within the scope of the appended claims.

I claim:

1. A fluid handling structure comprising:
    a planar substrate of a first dielectric material and having a principal surface;
    a plurality of channel structures formed on the principal surface, each channel structure extending from the principal surface and being of a second differing dielectric material, and defining a fluid-carrying channel between the channel structure and the principal surface; and
    a layer of polymer overlying and in contact with each of the channel structures.

2. The structure of claim 1, wherein the first dielectric material is selected from the group consisting of PYREX, fused silica, and plastic.

3. The structure of claim 1, wherein the second dielectric material is selected from the group consisting of silicon oxynitride, silicon nitride, aluminum oxide, silicon dioxide, titanium nitride, titanium oxide, silicon carbide, diamond, and polyamide.

4. The structure of claim 1, wherein each of the channel structures has a wall thickness of less than 5 $\mu$m.

5. The structure of claim 1, wherein at least one of the channel structures includes an internal support post extending vertically in the channel from the principal surface to a roof of the channel structure.

6. The structure of claim 1, further comprising an anodic bond attaching each channel structure to the principal surface.

7. The structure of claim 1, wherein each of the channels is less than 500 $\mu$m wide and 100 $\mu$m in height.

8. The structure of claim 1, further comprising at least one through-hole defined in the substrate and communicating with one of the channels.

9. The structure of claim 8, further comprising an electrode on a backside surface of the planar substrate and extending into the through-hole.

10. The structure of claim 1, further comprising a mesa of a third material formed on the principal surface of the substrate and extending over at least part of an outer surface of one of the channel structures.

11. The structure of claim 10, further comprising a resistive heating trace formed on an outer surface of the mesa.

12. The structure of claim 1, further comprising a layer of a dielectric material on the principal surface of the substrate and extending over at least part of an outer surface of at least one of the channel structures.

13. The structure of claim 1, further comprising at least two electrodes on an backside surface of the planar substrate.

14. A fluid handling structure comprising:
    a planar substrate of a first dielectric material and having a principal surface; and
    a plurality of channel structures formed on the principal surface, each channel structure extending from the principal surface and being of a second differing dielectric material, and defining a fluid-carrying channel between the channel structure and the principal surface;
    wherein at least one of the channel structures includes an internal support post extending vertically in the channel from the principal surface to a roof of the channel structure.

15. A fluid handling structure comprising:
    a planar substrate of a first dielectric material and having a principal surface;
    a plurality of channel structures formed on the principal surface, each channel structure extending from the principal surface and being of a second differing dielectric material, and defining a fluid-carrying channel between the channel structure and the principal surface;
    at least one through-hole defined in the substrate and communicating with one of the channels; and
    an electrode on a backside surface of the planar substrate and extending into the through-hole.

16. A fluid handling structure comprising:
    a planar substrate of a first dielectric material and having a principal surface;
    a plurality of channel structures formed on the principal surface, each channel structure extending from the principal surface and being of a second differing dielectric material, and defining a fluid-carrying channel between the channel structure and the principal surface;
    wherein the second dielectric material is selected from the group consisting of silicon oxynitride, silicon nitride, aluminum oxide, titanium nitride, titanium oxide, silicon carbide, diamond, and polyamide.

* * * * *